US012558009B2

(12) United States Patent
Lee et al.

(10) Patent No.: US 12,558,009 B2
(45) Date of Patent: Feb. 24, 2026

(54) METHOD FOR CALCULATING CALIBRATION SENSITIVITY OF SENSOR FOR INSERTION INTO BODY

(71) Applicant: I-SENS, INC., Seoul (KR)

(72) Inventors: David Lee, Seoul (KR); Ji Seon Nah, Seoul (KR); Jung Hee Seo, Seoul (KR); Young Jea Kang, Seoul (KR)

(73) Assignee: I-SENS, INC., Seoul (KR)

( * ) Notice: Subject to any disclaimer, the term of this patent is extended or adjusted under 35 U.S.C. 154(b) by 716 days.

(21) Appl. No.: 17/909,072

(22) PCT Filed: Mar. 10, 2021

(86) PCT No.: PCT/KR2021/002977
§ 371 (c)(1),
(2) Date: Sep. 2, 2022

(87) PCT Pub. No.: WO2021/182871
PCT Pub. Date: Sep. 16, 2021

(65) Prior Publication Data
US 2023/0039204 A1     Feb. 9, 2023

(30) Foreign Application Priority Data

Mar. 13, 2020     (KR) ........................ 10-2020-0031535

(51) Int. Cl.
*A61B 5/1495*     (2006.01)
*A61B 5/145*     (2006.01)
*A61B 5/155*     (2006.01)

(52) U.S. Cl.
CPC ........ *A61B 5/1495* (2013.01); *A61B 5/14503* (2013.01); *A61B 5/155* (2013.01)

(58) Field of Classification Search
CPC ... A61B 5/1495; A61B 5/145; A61B 5/14503; A61B 5/155; A61B 5/15; A61B 5/00;
(Continued)

(56) References Cited

U.S. PATENT DOCUMENTS

| 5,706,072 A | 1/1998 | Kawamura |
| 7,029,444 B2 | 4/2006 | Shin et al. |

(Continued)

FOREIGN PATENT DOCUMENTS

| CN | 101226698 | 7/2008 |
| CN | 106358291 | 1/2017 |

(Continued)

OTHER PUBLICATIONS

Notice of Allowance dated Dec. 23, 2021 for Korean Patent Application No. 10-2020-0031535 and its English translation from Global Dossier.

(Continued)

*Primary Examiner* — Mohamed Charioui
(74) *Attorney, Agent, or Firm* — WOMBLE BOND DICKINSON (US) LLP

(57) ABSTRACT

The present disclosure relates to a method for calculating the calibration sensitivity of a sensor for insertion into the body and, more particularly, to a method for calculating calibration sensitivity, wherein a biometric value of a user can be accurately calibrated by overcoming an error in a biometric value measured through a sensor for insertion into the body, or an error in a reference biometric value measured through a biometric information measurement device, by storing past sensitivities and using at least one of the past sensitivities and a currently calculated sensitivity to calculate a calibration sensitivity of the sensor for insertion into the body, and the calibration sensitivity of the sensor for insertion into the body can be accurately calculated, even if there is an error in the reference biometric value or the reference biometric value temporarily deviates from the range of normal biometric values of the user, by determining whether the reference biometric value used to calculate the calibration sensitivity is within an allowable range.

11 Claims, 10 Drawing Sheets

(58) Field of Classification Search

CPC ........ A61B 2560/0223; A61B 2560/02; A61B 2560/00; A61B 5/14865; A61B 5/14532; A61B 5/72

See application file for complete search history.

(56) References Cited

U.S. PATENT DOCUMENTS

| | | | |
|---|---|---|---|
| 7,996,158 | B2 | 8/2011 | Hayter et al. |
| 11,199,556 | B2 | 12/2021 | Shimizu |
| 11,311,217 | B2 | 4/2022 | Ajemba et al. |
| 2008/0312844 | A1 | 12/2008 | Hayter et al. |
| 2010/0162786 | A1 | 7/2010 | Keenan et al. |
| 2011/0021889 | A1* | 1/2011 | Hoss .................... A61B 5/7221 |
| | | | 600/310 |
| 2012/0173200 | A1* | 7/2012 | Breton ................... H04B 17/00 |
| | | | 702/182 |
| 2012/0265036 | A1 | 10/2012 | Estes et al. |
| 2014/0121480 | A1* | 5/2014 | Budiman ........... A61B 5/14546 |
| | | | 600/309 |
| 2015/0351673 | A1* | 12/2015 | Vanslyke ............. A61B 5/1473 |
| | | | 600/301 |
| 2017/0071512 | A1 | 3/2017 | Garcia et al. |
| 2019/0357827 | A1* | 11/2019 | Li ...................... A61B 5/14503 |
| 2020/0305772 | A1 | 10/2020 | Oh et al. |

FOREIGN PATENT DOCUMENTS

| | | |
|---|---|---|
| CN | 109211987 | 1/2019 |
| JP | 2005-524463 | 8/2005 |
| JP | 2019-013750 | 1/2019 |
| JP | 2019-506201 | 3/2019 |
| KR | 10-2019-0057759 | 5/2019 |
| KR | 10-2019-0088847 | 7/2019 |
| KR | 10-2019-0112088 | 10/2019 |

OTHER PUBLICATIONS

International Search Report for PCT/KR2021/002977 mailed on Jun. 14, 2021 and its English translation from WIPO (now published as WO 2021/182871).

Written Opinion of the International Searching Authority for PCT/KR2021/002977 mailed on Jun. 14, 2021 and its English translation by Google Translate (now published as WO 2021/182871).

European Search Report dated Jan. 17, 2024 for European Patent Application No. 21768123.8.

Office Action (1st) dated Jul. 1, 2025 for Chinese Patent Application No. 202180017135.7 and its English translation from Global Dossier.

Office Action dated Mar. 25, 2025 for Japanese Patent Application No. 2022-552914 and its English translation by Google Translate.

Office Action dated Sep. 24, 2024 for Japanese Patent Application No. 2022-552914 and its English translation from Global Dossier.

* cited by examiner

[Fig. 1]
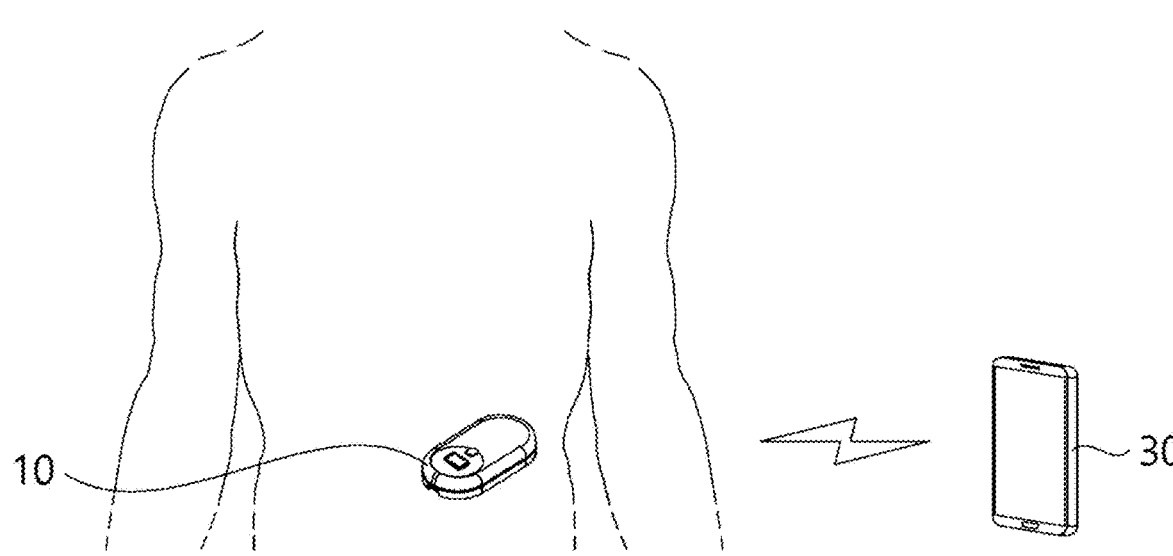
10
30

[Fig. 2]
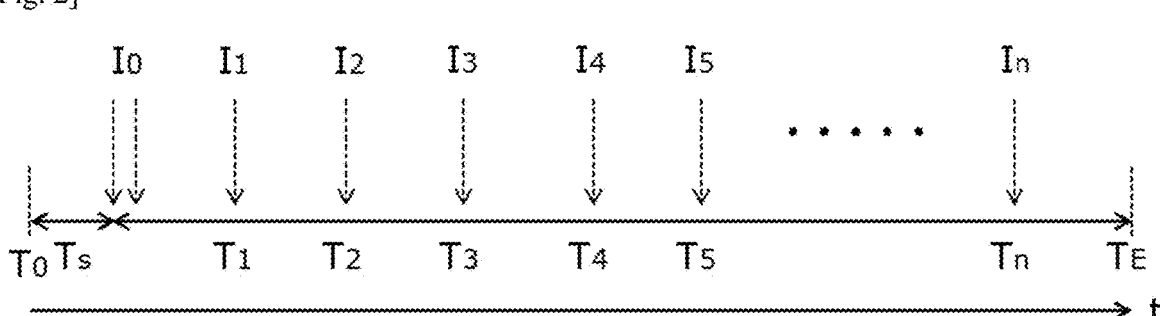

[Fig. 3]
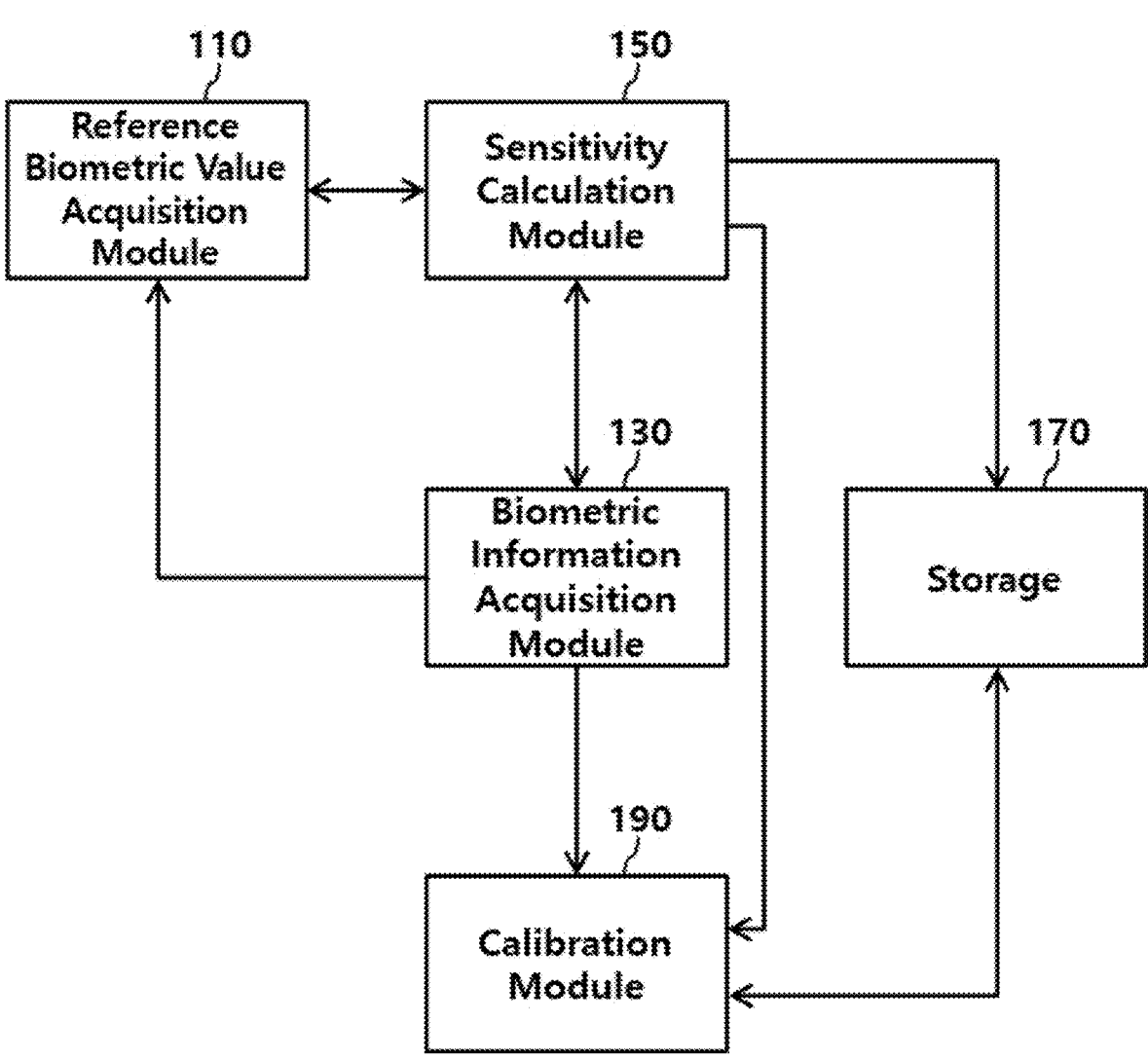

Figure 5:
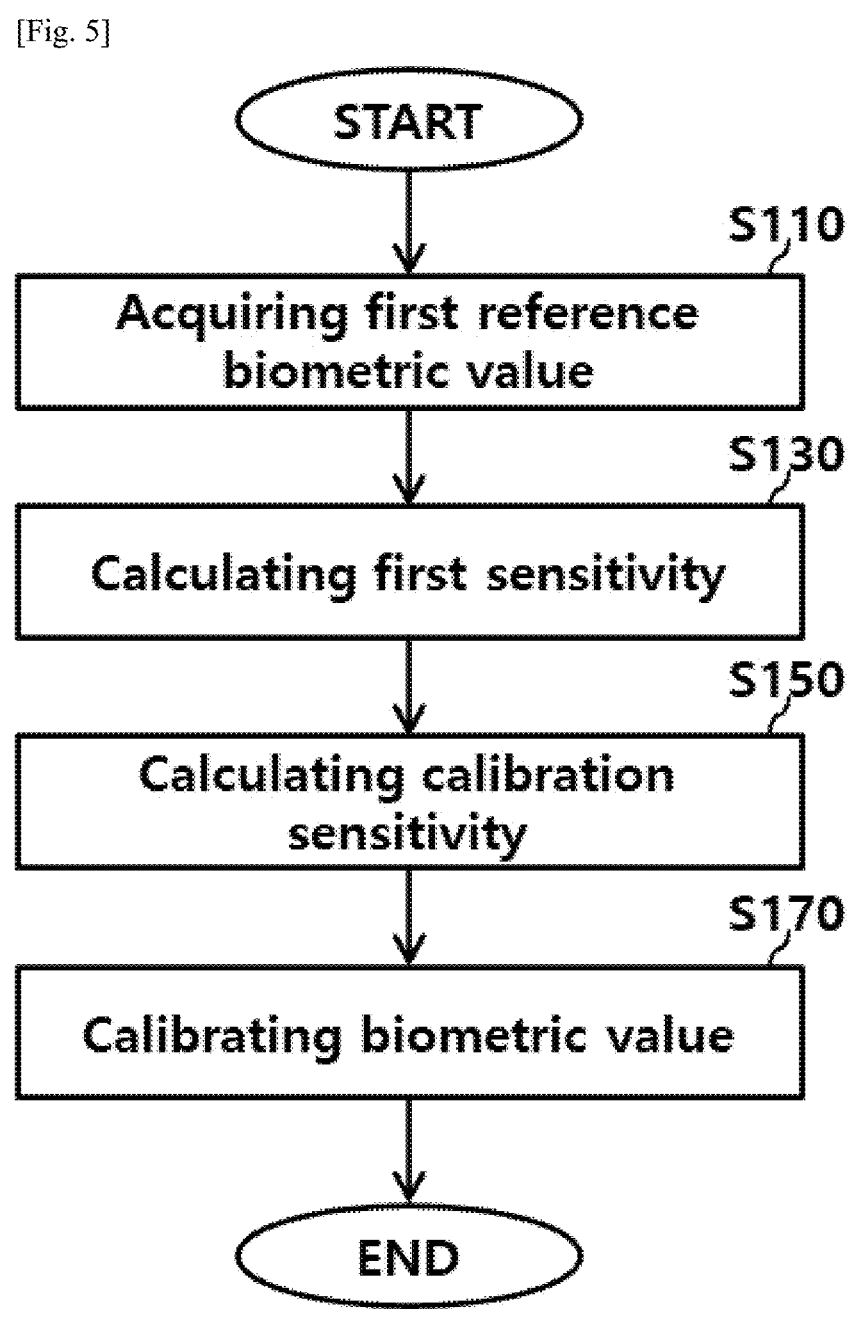

```
                    ┌─────────────┐
                    │    START    │
                    └──────┬──────┘
                           │
                           ▼                    S110
            ┌──────────────────────────────┐
            │   Acquiring first reference   │
            │        biometric value        │
            └──────────────┬───────────────┘
                           │
                           ▼                    S130
            ┌──────────────────────────────┐
            │   Calculating first sensitivity │
            └──────────────┬───────────────┘
                           │
                           ▼                    S150
            ┌──────────────────────────────┐
            │      Calculating calibration   │
            │            sensitivity         │
            └──────────────┬───────────────┘
                           │
                           ▼                    S170
            ┌──────────────────────────────┐
            │   Calibrating biometric value  │
            └──────────────┬───────────────┘
                           │
                           ▼
                    ┌─────────────┐
                    │     END     │
                    └─────────────┘
```

[Fig. 6]

|  | Sensitivity | Calibration Sensitivity | Generation Time (Calibration Sensitivity) |
|---|---|---|---|
| n | 0.05 | 0.51 | 2020.01.27. 16:23 |
| n-1 | 0.43 | 0.47 | 2020.01.28. 16:31 |
| | ⋮ | ⋮ | ⋮ |
| 5 | 0.81 | 0.59 | 2020.02.26. 16:15 |
| 4 | 0.63 | 0.60 | 2020.02.27. 09:26 |
| 3 | 0.55 | 0.58 | 2020.02.28. 09:33 |
| 2 | 0.49 | 0.56 | 2020.03.01. 09:29 |
| 1 | 0.51 | 0.54 | 2020.03.02. 09:13 |

[Fig. 7]
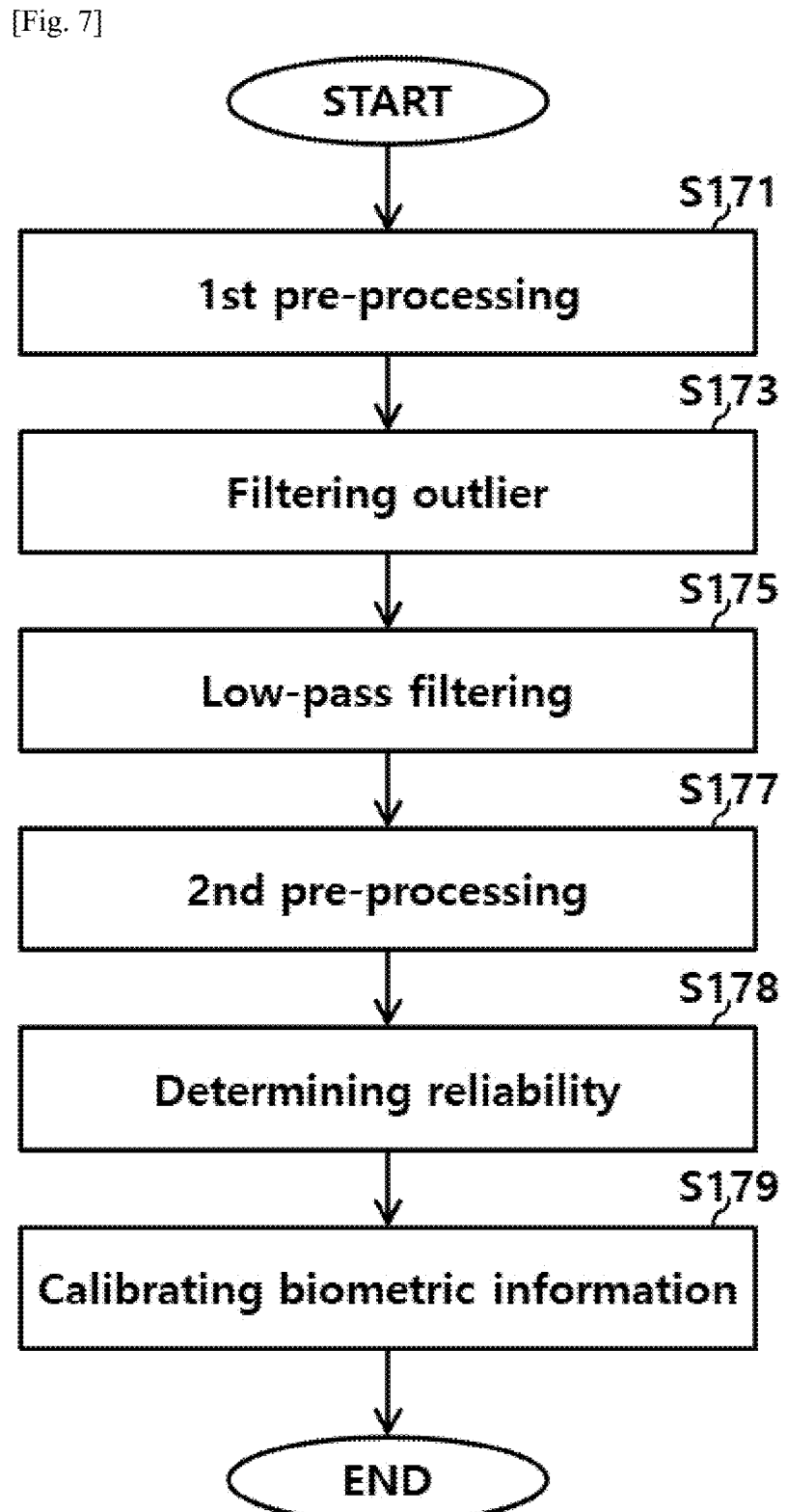

[Fig. 8]

[Fig. 9]
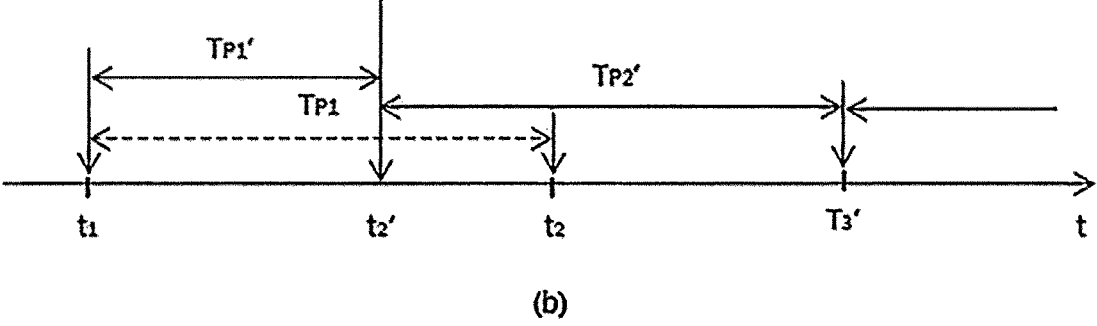
(a)
(b)

[Fig. 10]
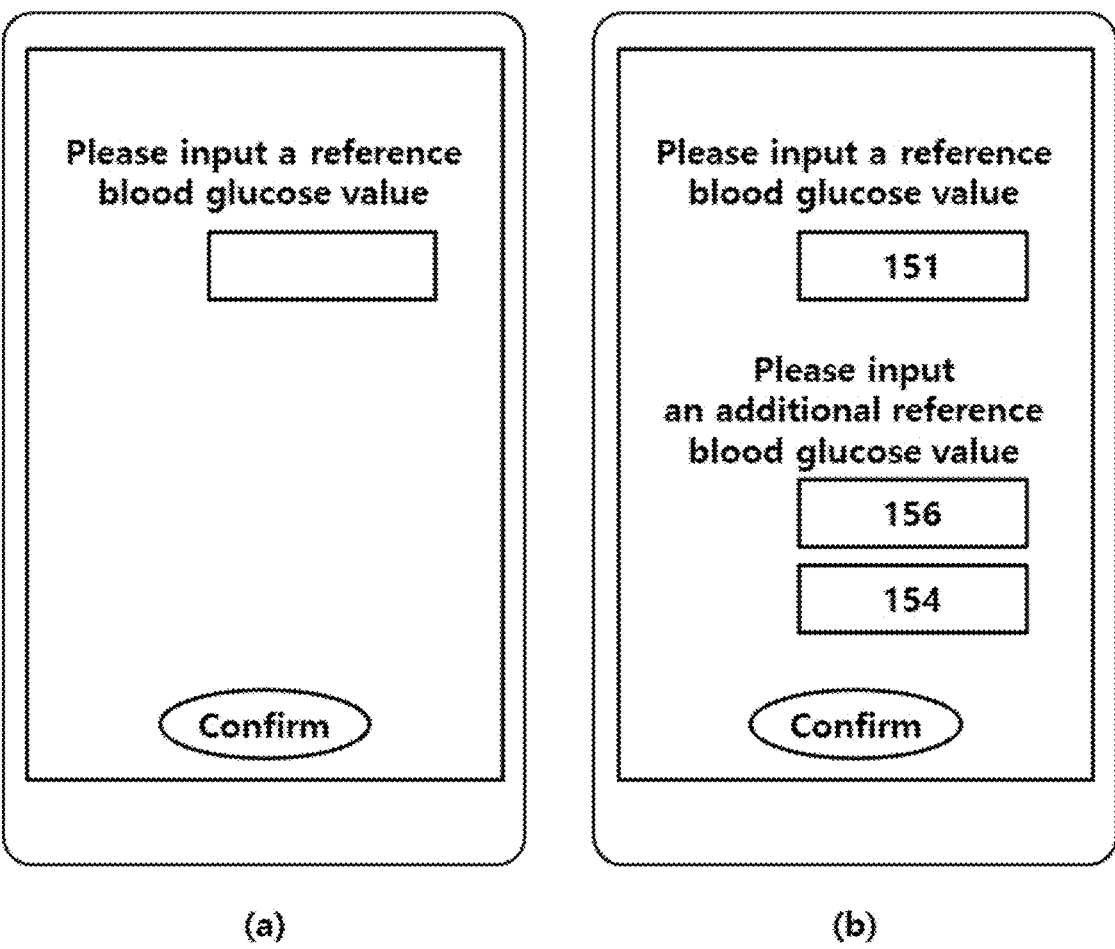

METHOD FOR CALCULATING CALIBRATION SENSITIVITY OF SENSOR FOR INSERTION INTO BODY

CROSS-REFERENCE TO RELATED APPLICATIONS

The present application is the U.S. National Phase of PCT Application No. PCT/KR2021/002977 filed on Mar. 10, 2021, which claims the priority to Korean Patent Application No. 10-2020-0031535 filed on Mar. 13, 2020, the entire contents of which are incorporated herein by reference.

TECHNICAL FIELD

The present disclosure relates to a method for calculating a calibration sensitivity of a sensor for insertion into a body, and more particularly, a method for calculating a calibration sensitivity of a sensor for insertion into a body, the method which, by storing past sensitivities and calculating a calibration sensitivity of the sensor for insertion into the body using at least one or more past sensitivities and a currently calculated sensitivity, can accurately calibrate a biometric value of a user by correcting an error in a biometric value measured through the sensor for insertion into the body or an error in a reference biometric value measured through a biometric information meter, and by determining whether the reference biometric value used when calculating the calibration sensitivity is within an allowable range, can accurately calculate the calibration sensitivity of the sensor for insertion into the body even if there is an error in the reference biometric value or even though the reference biometric value temporarily deviates from a normal biometric value range of the user.

BACKGROUND

Diabetes is a chronic medical condition that is common in modern people, and in the Republic of Korea, there are 2 million diabetes patients, about 5% of the total population.

Diabetes occurs when the absolute level of the sugar level in blood is high due to the absolute deficiency or relative insufficiency of insulin, produced by the pancreas, caused by various reasons such as obesity, stress, poor eating habits, and inherited hereditary factors and imbalance regarding glucose in the blood.

The blood usually contains a certain concentration of glucose, and tissue cells gain energy from the glucose.

However, when the glucose is increased excessively more than needed, the glucose cannot be properly stored in the liver, muscle, or adipose tissue and is accumulated in the blood, because of this, patients with diabetes maintain a much higher blood glucose level than normal people, and as excessive blood glucose passes through the tissues and is discharged into the urine, it results in deficiency of glucose, which is absolutely necessary for all tissues of the body, thereby causing abnormalities in respective body tissues.

Diabetes is characterized by substantial absence of subjective symptoms at the beginning of the condition, when diabetes progresses, diabetes-specific symptoms such as overdrink, overeat, polyuria, weight loss, weariness, skin itchiness, and lower ability of naturally healing on injury on hands and feet are shown, and further progression of diabetes leads to complications such as visual disturbances, hypertension, kidney disease, paralysis, periodontal disease, muscle spasms and neuralgia, as well as gangrene.

In order to diagnose diabetes beforehand and manage to prevent the progression of diabetes into complications associated therewith, systematic blood glucose measurement and treatment should be performed.

Diabetes need to constantly measure blood glucose for management, so the demand for devices related to blood glucose measurement is steadily increasing. It has been confirmed through various studies that, when diabetic patients strictly control the management of blood glucose, the incidence of complications of diabetes is significantly reduced. Accordingly, it is very important for diabetic patients to measure blood glucose regularly for blood glucose management.

In general, a blood-gathering-type biometric information meter (a finger prick type method) is mainly used for blood glucose control in diabetic patients. This blood-gathering-type biometric information meter helps diabetic patients to manage their blood glucose, but because only the result at the time of measurement is displayed, there is a problem that it is difficult of precisely monitoring the blood glucose level that changes frequently. In addition, since the blood-gathering-type biometric information meter needs to collect blood every time to measure blood glucose frequently during the day, there is a problem in that the burden of blood collection is huge for diabetic patients.

Diabetics patients generally experience hyperglycemia and hypoglycemia, and an emergency may occur in the hypoglycemic conditions. Hypoglycemia occurs when sugar content is not kept for a long time, and the patients may become unconscious or die in a worst case. Accordingly, rapid discovery of the hypoglycemic condition is critically important for diabetics. The blood-gathering-type biometric information measuring device intermittently measuring glucose have limited ability to accurately measure blood glucose levels.

Recently, to overcome such a drawback of the blood-gathering-type biometric information measuring device, continuous glucose monitoring systems (CGMSs) inserted into the human body to measure a blood glucose level every few minutes have been developed, and therefore easily perform the management of diabetics and responses to an emergency situation.

The continuous glucose monitoring system includes a sensor transmitter configured to be attachable to a body part of a user and generate biometric information by extracting body fluid, a communication terminal configured to calculate a biometric value from the received biometric information and output it, and so on. The sensor transmitter has a sensor for continuous blood glucose measurement, of which part is inserted to the human body, and the sensor extracts the body fluid of the user for a certain period, for example, fifteen (15) days, in a state of being inserted to the human body. The sensor transmitter periodically generates biometric information from the extracted body fluid, and a blood glucose management application is installed to the communication terminal, periodically receives the biometric information from the sensor transmitter, and calibrates the received biometric information and outputs it to the user.

The sensor of the sensor transmitter is continuously inserted in the skin for a certain period of use, but the sensitivity of the sensor varies depending on the body part where the sensor is inserted, and even if a location of the body part where the sensor is inserted is the same, the sensitivity of the sensor inserted into the skin is changed over time. Accordingly, the biometric information generated by the sensor transmitter may have an error, and the biometric value of the user must be calibrated by applying a calibration sensitivity to the generated biometric information.

In order to provide an accurate biometric value to the user, the biometric information received from the sensor transmitter should be initially calibrated, and thereafter, it should be calibrated continuously at regular calibration cycles during the use period of the sensor transmitter. More specifically, at the time of the initial calibration, the reference biometric value measured through a separate biometric information meter is input to the communication terminal to calibrate the biometric information received from the sensor transmitter as the reference biometric value, and thereafter, the biometric information received from the sensor transmitter should be calibrated with the reference biometric value measured through the biometric information meter continuously at every calibration cycle during the use period of the sensor transmitter.

In order to calibrate the biometric information measured by the sensor transmitter, the calibration sensitivity is calculated, and the conventional calibration sensitivity is calculated from the ratio of the biometric information measured by the sensor transmitter and the reference biometric value measured by the biometric information meter. For example, if the biometric information measured at a first time point by the sensor transmitter is 5 and the reference biometric value measured through the test strip by the biometric information meter is 100, the calibration sensitivity is calculated as 0.05 (5/100). The biometric information measured by the sensor transmitter after the first time point is calibrated using the calibration sensitivity.

The biometric information meter or the test strip has its own allowable error or tolerance, and a certain error also exists in the biometric information measured by the sensor transmitter. Accordingly, due to an error of the reference biometric value measured by the blood glucose meter or an error of the biometric information measured by the sensor transmitter, the calibration sensitivity calculated from the reference biometric value and the biometric information also has an error. There is a problem in that a large error occurs in the calibrated biometric value due to the error of the calibration sensitivity, and the biometric value of the user cannot be accurately monitored.

DETAILED DESCRIPTION OF DISCLOSURE

Technical Problem

To solve the problem of the conventional method for calculating a calibration sensitivity of a sensor for insertion into a body described above, the purpose of the present disclosure may be for providing a method for calculating a calibration sensitivity of a sensor for insertion into a body, the method which stores past sensitivities and accurately calculates a calibration sensitivity of the sensor for insertion into the body using the past sensitivity and a currently calculated sensitivity.

Another purpose of the present disclosure is for providing a method for calculating a calibration sensitivity of a sensor for insertion into a body, the method which, by determining whether a reference biometric value used when calculating a calibration sensitivity is within an allowable range, can accurately calculate the calibration sensitivity of the sensor for insertion into the body using the reference biometric value within the allowable range.

Solution to Problem

To accomplish the purpose of the present disclosure, a method for calculating a calibration sensitivity of a sensor for insertion into a body comprises: acquiring a first reference biometric value indicating a biometric state of a user at a first time point, and calculating a first sensitivity from a ratio of biometric information measuring the biometric state of the user using the sensor for insertion into the body at the first time point and the first reference biometric value; retrieving past sensitivity information which has been pre-stored and used before the first time point; and calculating the calibration sensitivity for calibrating the biometric information measured through the sensor for insertion into the body after the first time point from the first sensitivity and the past sensitivity information.

Here, the past sensitivity information is at least one calibration sensitivity which was used before the first time point or at least one sensitivity which was calculated before the first time point.

Here, the past sensitivity information is at least one calibration sensitivity which was used continuously just before the first time point or at least one sensitivity which was calculated just before the first time point.

Here, the past sensitivity information is at least one calibration sensitivity randomly selected from calibration sensitivities which had been used for a past set time period based on the first time point or at least one sensitivity randomly selected from sensitivities which had been calculated for the past set time period based on the first time point.

Preferably, the calculating of the first sensitivity comprises: acquiring the first reference biometric value of the user indicating the biometric state of the user through a test strip at the first time point; determining the biometric information measured through the sensor for insertion into the body at the first time point; and calculating the first sensitivity based on a ratio of the biometric information and the first reference biometric value.

Here, a difference between a biometric value of the user, calculated from the biometric information using the past calibration sensitivity, and the first reference biometric value is calculated, and if the difference is out of a threshold range, the acquired first reference biometric value is removed.

Preferably, in the acquiring of the first reference biometric value, one calibration mode among a first calibration mode and a second calibration mode is selected based on whether the difference between the biometric value of the user, calculated from the biometric information using the past calibration sensitivity, and the first reference biometric value is out of the threshold range.

Here, when the difference is within the threshold range, the first calibration mode is selected, and in the first calibration mode, one reference biometric value measured through the test strip at the first time point is acquired as the first reference biometric value.

Here, when the difference is out of the threshold range, the second calibration mode is selected, and in the second calibration mode, one or more additional reference biometric values are additionally acquired through the test strip continuously after the first time point, and the first reference biometric value is acquired from the reference biometric value acquired at the first time point and an average value of the one or more additional reference biometric values.

Here, the calibration sensitivity is calculated as an average value of the first sensitivity and the past sensitivity information.

Here, when a new reference biometric value is acquired after the first time point, the first sensitivity is stored and a calibration sensitivity is newly calculated using the stored first sensitivity as a past sensitivity.

Preferably, the method further comprises determining whether a calibration cycle set after the first time point arrives, and when the set calibration cycle arrives, outputting a request message for requesting to input the new reference biometric value, wherein, when the new reference biometric value is acquired in response to the request message, the first sensitivity is stored and the calibration sensitivity is newly calculated using the stored first sensitivity as the past sensitivity.

Advantageous Effects of Invention

A method for calculating a calibration sensitivity of a sensor for insertion into a body according to an embodiment of the present disclosure has the following effects.

A method for calculating a calibration sensitivity of a sensor for insertion into a body according to an embodiment of the present disclosure, by storing past sensitivities and calculating a calibration sensitivity of the sensor for insertion into the body using at least one or more past sensitivities and a currently calculated sensitivity, can accurately calibrate a biometric value of a user by correcting an error in a biometric value measured through the sensor for insertion into the body or an error in a reference biometric value measured through a biometric information meter.

Additionally, a method for calculating a calibration sensitivity of a sensor for insertion into a body according to an embodiment of the present disclosure, by determining whether the reference biometric value used when calculating the calibration sensitivity is within an allowable range, can accurately calculate the calibration sensitivity of the sensor for insertion into the body even if there is an error in the reference biometric value or even though the reference biometric value temporarily deviates from a normal biometric value range of the user.

BRIEF DESCRIPTION OF THE DRAWINGS

FIG. 1 is a schematic diagram for illustrating a continuous blood glucose measurement system according to an embodiment of the present disclosure.

FIG. 2 is a diagram for explaining an example of an input of initial calibration information or periodic calibration information.

FIG. 3 is a functional block diagram for illustrating an apparatus for calculating a sensitivity of a sensor for insertion into a body according to an embodiment of the present disclosure.

FIG. 4 is a functional block diagram for illustrating an example of a reference biometric value acquisition module according to an embodiment of the present invention.

FIG. 5 is a flowchart for explaining a method of calculating a calibration sensitivity of a sensor for insertion into a body according to an embodiment of the present disclosure.

FIG. 6 shows an example of past sensitivity information stored in a storage.

FIG. 7 is a flow chart for illustrating a pre-processing process of biometric information.

FIG. 8 is a flowchart for explaining a method for obtaining a first reference biometric value according to an embodiment of the present disclosure.

FIG. 9 is a diagram for explaining a time point when a calibration sensitivity is generated.

FIG. 10 illustrates an example of a user interface screen displayed on a user terminal to select a calibration mode according to another embodiment of the present disclosure.

DESCRIPTION OF EMBODIMENTS OF DISCLOSURE

The technical terms used in the present disclosure are only for the purpose of describing exemplary embodiments, and they are not intended to limit the present invention. Also, unless otherwise defined, all technical terms used herein should be construed as having the same meaning as commonly understood by those skilled in the art, and should not be interpreted as being excessively inclusive or excessively restrictive. In addition, when a technical term used herein is an erroneous technical term that does not accurately represent the idea of the present invention, it should be understood as replacing the term by a technical term which can be properly understood by those skilled in the art.

Further, singular expressions used in the present specification include plural expressions unless they have definitely opposite meanings. In the present application, it shall not be construed that terms, such as "including" or "comprising", various constituent elements or steps described in the specification need to be all essentially included, and it shall be construed that some constituent elements or steps among the various constituent elements or steps may be omitted, or additional constituent elements or steps may be further included.

Also, it should be noted that the accompanying drawings are merely illustrated to easily explain the spirit of the invention, and therefore, they should not be construed to limit the spirit of the invention by the accompanying drawings.

FIG. 1 is a schematic diagram for illustrating a continuous blood glucose measurement system according to an embodiment of the present disclosure.

Referring to FIG. 1, the continuous blood glucose measurement system (1) according to an embodiment of the present disclosure comprises a sensor transmitter (10) and a communication terminal (30).

The sensor transmitter (10) is attachable to human body and, when the sensor transmitter (10) is attached to the human body, an end portion of a sensor of the sensor transmitter (10) is inserted into skin to periodically extract body fluid of the human body and measure blood glucose.

The communication terminal (30) is a terminal configured to receive blood glucose information from the sensor transmitter (10), calibrate the received blood glucose information, and output the generated blood glucose value to a user, and for example, the communication terminal (30) may be a portable terminal (such as smartphone, tablet PC, or notebook and so on) configured to communicate with the sensor transmitter (10). However, the communication terminal (30) is not limited thereto, and may be any type of a terminal to which has a communication function and program or application can be installed.

The sensor transmitter (10) transmits the blood glucose information in response to request of the communication terminal (30) or at predetermined times periodically, and for data communication between the sensor transmitter (10) and the communication terminal (30), the sensor transmitter (10) and the communication terminal (30) are communicationally connected to each other over a wire by an USB cable and so on or communicationally connected in an wireless communication means such as infrared communication, NFC communication, Bluetooth, etc.

More specifically, when the communication between the sensor transmitter (10) and the communication terminal (30) is connected, after stabilization of the sensor transmitter (10), an initial calibration sensitivity is calculated using a reference blood glucose value measured through a separate biometric information meter (not shown), and initial calibration on blood glucose information is performed using the initial calibration sensitivity. Thereafter, the communication terminal (30) calibrates the blood glucose information received from the sensor transmitter (10) with the initial calibration sensitivity, and outputs the corrected blood glucose value to the user.

In order to accurately calibrate blood glucose information measured by the sensor transmitter (10), the communication terminal (30) uses a reference blood glucose value measured through a separate biometric information meter periodically during the period of use of the sensor transmitter (10) to calculate a new calibration sensitivity, calibrates the blood glucose information received from the sensor transmitter using the new calibration sensitivity to calculate a blood glucose value, and output the calculated blood glucose value to the user.

FIG. 2 is a diagram for explaining an example of an input of initial calibration information or periodic calibration information, and the calibration information is a reference blood glucose value of a user measured with a test strip through a biometric information meter. Referring to FIG. 2, a sensor transmitter is stabilized from time $(T_0)$ when the communication between the sensor transmitter and the communication terminal is connected until set stabilization time $(T_S)$ elapses.

When the stabilization of the sensor transmitter is completed, initial calibration information $(I_0)$ is input to the communication terminal. Here, the initial calibration information $(I_0)$ may be inputted multiple times to accurately calibrate calibration sensitivity. The communication terminal calculates an initial calibration sensitivity by using the initial calibration information and blood glucose information measured by the sensor transmitter, and calculates a blood glucose value of the user by calibrating the blood glucose information received from the sensor transmitter using the initial calibration sensitivity.

New calibration information $(I_1, I_2, I_3, I_4 \ldots)$ is inputted to the communication terminal periodically, preferably, every twelve (12) hours, one (1) day, etc., after the completion of stabilization of the sensor transmitter until an expiration time point $(T_E)$ of a use period of the sensor transmitter, and the communication terminal calculates a new calibration sensitivity which is to be used to calibrate blood glucose information received from the sensor transmitter from a time point when new calibration information is inputted every time new calibration information is inputted and calculates a blood glucose value of the user by calibrating the blood glucose information received from the sensor transmitter using the new correction sensitivity.

According to a field to which the present disclosure is applied, blood glucose information is an example of biometric information, a blood glucose value calculated from the blood glucose information is an example of a biometric value, and a reference blood glucose value used to calculate a calibration sensitivity is an example of a reference biometric value.

FIG. 3 is a functional block diagram for illustrating an apparatus for calculating a sensitivity of a sensor for insertion into a body according to an embodiment of the present disclosure.

Here, a sensitivity calculation device may be implemented in a communication terminal, and, according to a field to which the present disclosure is applied, may be implemented in a sensor transmitter.

Looking more in detail with reference to FIG. 3, an acquisition module (110) acquires a first reference biometric value from a reference biometric value measured through a biometric information meter at the request of the user at every set calibration period or regardless of the calibration period.

On the other hand, a biometric information acquisition module (130) continuously receives biometric information from the sensor transmitter.

When the first reference biometric value is acquired, a sensitivity calculation module (150) calculates a first sensitivity from the biometric information received from the sensor transmitter and the first reference biometric value, and calculates a calibration sensitivity, which is used to calibrate biometric information, from the first sensitivity and at least one or more of past sensitivity information stored in a storage (170). A sensitivity calculation module (150) stores and manages information on a new sensitivity, a new calibration sensitivity, and a time point when the new calibration sensitivity is calculated, in the storage unit 170 every time when a new calibration sensitivity is calculated.

A calibration module (190) determines whether a new calibration sensitivity is newly stored in the storage (170), when the new calibration sensitivity is newly stored, calibrates biometric information received from the sensor transmitter using the new calibration sensitivity to calculate a biometric value, and outputs information regarding the calculated biometric value to the user through an output module (not shown) such as a display, a speaker, and so on.

Preferably, the reference biometric value acquisition module (110) calculates difference between a measured biometric value calculated using a past calibration sensitivity from the biometric information measured by the sensor transmitter and a reference biometric value measured at the same time by the biometric information meter, and acquires a first reference biometric value differently depending on whether the difference between the measured biometric value and the reference biometric value is out of a threshold range.

Figure 4:
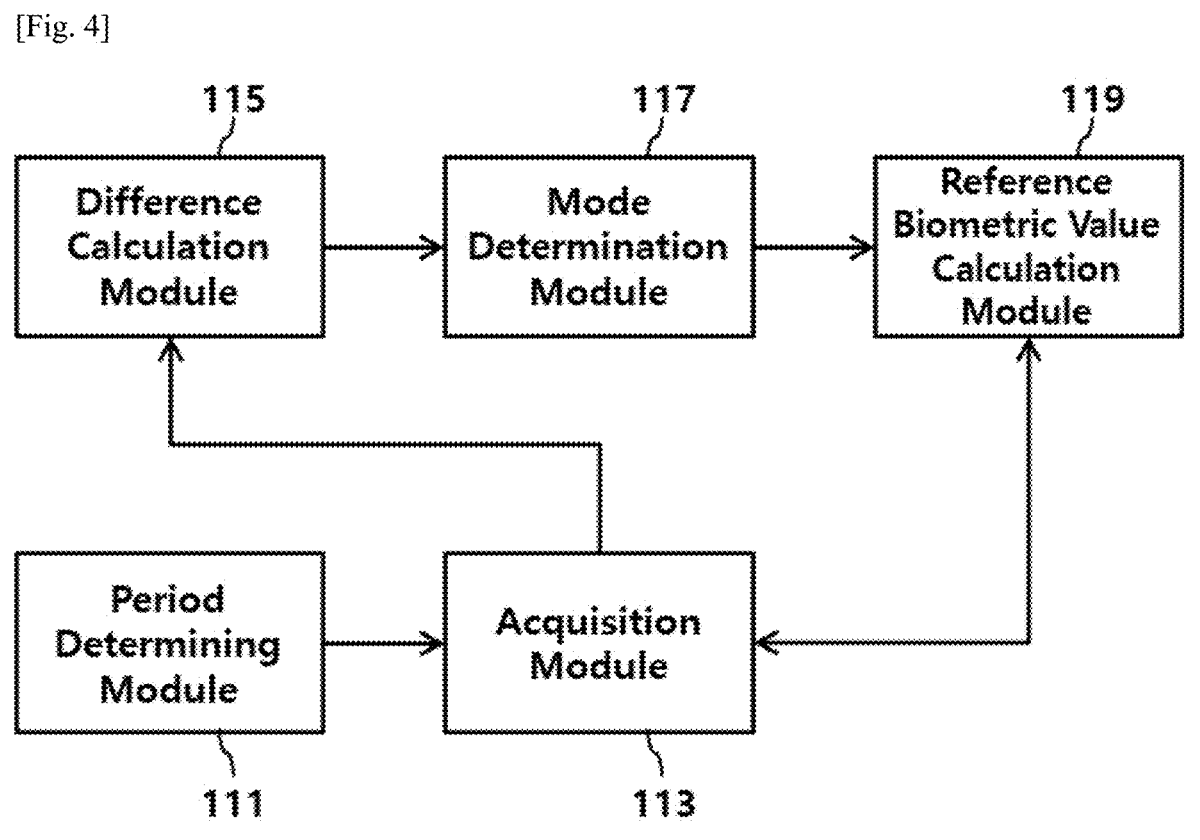

FIG. 4 is a functional block diagram for illustrating an example of a reference biometric value acquisition module according to an embodiment of the present invention.

Looking more in detail with reference to FIG. 4, a period determining module (111) determines whether a set calibration period reaches.

When the set calibration period reaches, an acquisition module (113) obtains a reference biometric value from a biometric information meter. Preferably, when the calibration period arrives, the acquisition module (113) may generate a request message for requesting an input of a reference biometric value at a first time point at which the calibration period arrives and output the request message to an output module. The acquisition module (113) may acquire an input which is directly inputted by a user through a user interface, and may receive an input from the biometric information meter through wireless or wired communication.

A difference calculation module (115) calculates a difference between a measured biometric value calculated from biometric information measured at a first time point by the sensor transmitter using a calibration sensitivity used up to the first time point and a reference biometric value at the first time point, and a mode determination module (117) determines a mode for obtaining a first reference biometric value based on whether the difference is within a threshold range. The mode determination module (117) chooses a first mode when the difference is within the threshold range, and chooses a second mode when the difference is out of the threshold range. Here, the threshold range may be a normal blood glucose range of a person or a blood glucose range between the highest blood glucose and the minimum blood glucose that a person can have.

A reference biometric value calculation module (119) calculates a first reference biometric value according to a mode chosen by the mode determining module (117). In the first mode, a reference biometric value at the first time point is used as a first reference biometric value. However, in the second mode, the reference biometric value calculation module (119) acquires at least one additional reference biometric value from a biometric information meter continuously after the first time point through the acquisition module (113), and calculates a first reference biological value with an average value of the reference biometric value acquired at the first time point and the additional reference biometric value.

FIG. 5 is a flowchart for explaining a method of calculating a calibration sensitivity of a sensor for insertion into a body according to an embodiment of the present disclosure.

Referring to FIG. 5 in more detail, a first reference biometric value indicating a biometric value of a user is obtained at a first time point using a biometric information meter (S110).

A first sensitivity is calculated from a ratio of biometric information measured by the sensor transmitter and the first reference biometric value at a time point corresponding to the first time point (S130).

At least one piece of pre-stored past sensitivity information that was used before the first time point is extracted, and a calibration sensitivity used to calibrate the biometric value of the user is calculated by applying the first sensitivity and the extracted past sensitivity information to biometric information measured by the sensor transmitter after the first time point (S150).

FIG. 6 shows an example of past sensitivity information stored in a storage, and as shown in FIG. 6, information on a sensitivity, a calibration sensitivity and time at which the calibration sensitivity was created is stored.

Here, past sensitivity information is at least one calibration sensitivity or sensitivity that was used before a first time point corresponding to a new calibration period, for example, a calibration cycle time point of after 09:13 on Mar. 2, 2020, and, preferably, it is characterized in that the past sensitivity information according to an embodiment of the present disclosure is a set number of calibration sensitivities or sensitivities that have been used continuously just before the first time point. For example, when the set number is two (2), a first calibration sensitivity and a second calibration sensitivity continuously used before the first time point may be used as past sensitivity information.

Preferably, it is characterized in that past sensitivity information according to another embodiment of the present disclosure is a set number of sensitivities or calibration sensitivities randomly selected from among sensitivities or calibration sensitivities used for a past set period based on the first time point. For example, when the set number is two (2) and the past set period is five (5) calibration cycles, two (2) sensitivities randomly selected from among the first to fifth sensitivities that were continuously used before the first time point may be used as the past sensitivity information.

Referring back to FIG. 5, a biometric value is calculated by applying a calibration sensitivity to biometric information measured by the sensor transmitter until a next calibration cycle arrives after the first time point or until a new reference biometric value is input by the user, and the corrected biometric value is outputted to the user (S170).

Here, when the calibration sensitivity is calculated using the past calibration sensitivity as the past sensitivity information, the calibration sensitivity can be more accurately calculated by considering a larger number of past sensitivities.

The biometric information measured by the sensor transmitter is pre-processed in the sensor transmitter, in the communication terminal, or in both the sensor transmitter and the communication terminal until it is calibrated to a biometric value, and FIG. 7 is a flow chart for illustrating a pre-processing process of biometric information.

Describing in more detail with reference to FIG. 7, if the measurement of the biometric information is performed by the sensor transmitter, a first pre-processing process of the measured biometric information is performed (S171). The first pre-processing process is one of processes for processing noise in the biometric information measured by the sensor transmitter. Preferably, the first pre-processing process can be performed by the sensor transmitter.

The first pre-processing process processes noise by calculating an average value of the measured biometric information, and, for example, the average value used in the first pre-processing process may be a trimmed average value which is calculated by removing a certain proportion of a top portion and a bottom portion of the measured biometric information and then calculating an average of the remaining information. However, it is not limited thereto, and any one of population mean, sample mean, weighted average, geometric average, harmonic average and generalized average can be used.

If the first pre-processing process is described as an example, one average value is calculated every ten (10) seconds by calculating an average value of thirty (30) pieces of biometric information converted into a digital signal using a trimmed average method. At this time, the upper seven (7) information and the lower seven (7) information among thirty (30) pieces of biometric information are removed, and an average value (A) of remaining sixteen (16) pieces of information is calculated. The calculated trimmed average value (A) may be generated in units of ten (10) seconds, and six (6) trimmed average values (A1 to A6) may be generated for one (1) minute. As the measured biometric information is processed through the first pre-processing process, noise in the measured biometric information can be removed.

Additionally, the first pre-processing process generates six (6) trimmed average values (A1 to A6) for one (1) minute, and generates a second trimmed average value (B1) using the generated six (6) trimmed average values (A1 to A6). At that time, the generated second trimmed average value (B1) is calculated by removing a maximum value and a minimum value among six (6) trimmed average values (A1 to A6) and calculating an average of remaining four values. Accordingly, the first pre-processing process generates one second trimmed average value (B) for one (1) minute.

In this way, an outlier processing filtering process is performed by finding and processing blood glucose information data that deviates from a predetermined condition in biometric information after the first pre-processing process (S173). In order to determine biometric information having an outlier value, whether the corresponding biometric information has a outlier value is determined using a plurality of pieces of previous biometric information with respect to one biometric information.

For example, in order to determine whether B6 among biometric information of B1 to B6 is outlier value biometric information, biometric information of B1 to B5 is used. In this example, an average slope or gradient of B1 to B5 may be used to determine whether B6 is outlier value biometric information, and when the value of B6 is out of a predetermined range from the average slope of B1 to B5, B6 may be determined as an outlier value.

Alternatively, a gradient change value of B1 to B5 can be used in order to determine whether B6 is outlier value biometric information or not, and if the value of B6 is out of a certain range from the gradient change value of B1 to B5, it is determined that B6 is an outlier value.

Alternatively, an average and standard deviation of B1 to B5 can be used in order to determine whether B6 is outlier value biometric information or not. Therefore, if the value of B6 is out of the standard deviation of B1 to B5, it is determined that B6 is an outlier value.

If it is determined that B6 is biometric information having an outlier value, that biometric information can be processed by being removed. However, the present disclosure is not limited thereto, and if necessary, B6 having an outlier value can be calibrated to be within a range which values of B1 to B5 have to be used.

The blood glucose information data which is processed by the outlier processing filtering can be further processed by low pass filtering (S175). The low pass filtering process may be a process for removing components corresponding to a high band and leaving components corresponding to a low band only.

A second pre-processing process can be performed to the blood glucose biometric information processed by the low pass filtering (S177). Unlike the first pre-processing process, the second pre-processing process is proceeded and performed by calculating an average value of the biometric information processed by the low pass filtering. In this embodiment, like the first pre-processing process, the second pre-processing process can use a trimmed average value.

After that, whether the blood glucose information data processed by the second pre-processing process can be trusted is determined (S178). This is a step for verifying whether the biometric information processed by the second pre-processing process can be trusted. In this step, verification data is generated using the biometric information processed by the low pass filtering process, and if the generated verification data is within a set range, it is determined that the biometric information processed by the second pre-processing process can be trusted.

If the biometric information data processed by the second pre-processing process is verified as data which can be trusted, the calibration to the verified biometric information is performed (S179).

However, if the biometric information processed by the second pre-processing process is not verified as data which can be trusted, a process of a linear regression filtering is performed to the biometric information processed by the second pre-processing process. The linear regression filtering process can change or transform a value of data using multiple past biometric information with reference to one biometric information among the biometric information data processed by the second pre-processing process. Therefore, if the biometric information is transformed by the linear regression filtering, the transformed biometric information can be recognized as data which can be trusted. The calibration to the biometric information which is recognized as data which can be trusted through the linear regression filtering is performed.

Figure 8:
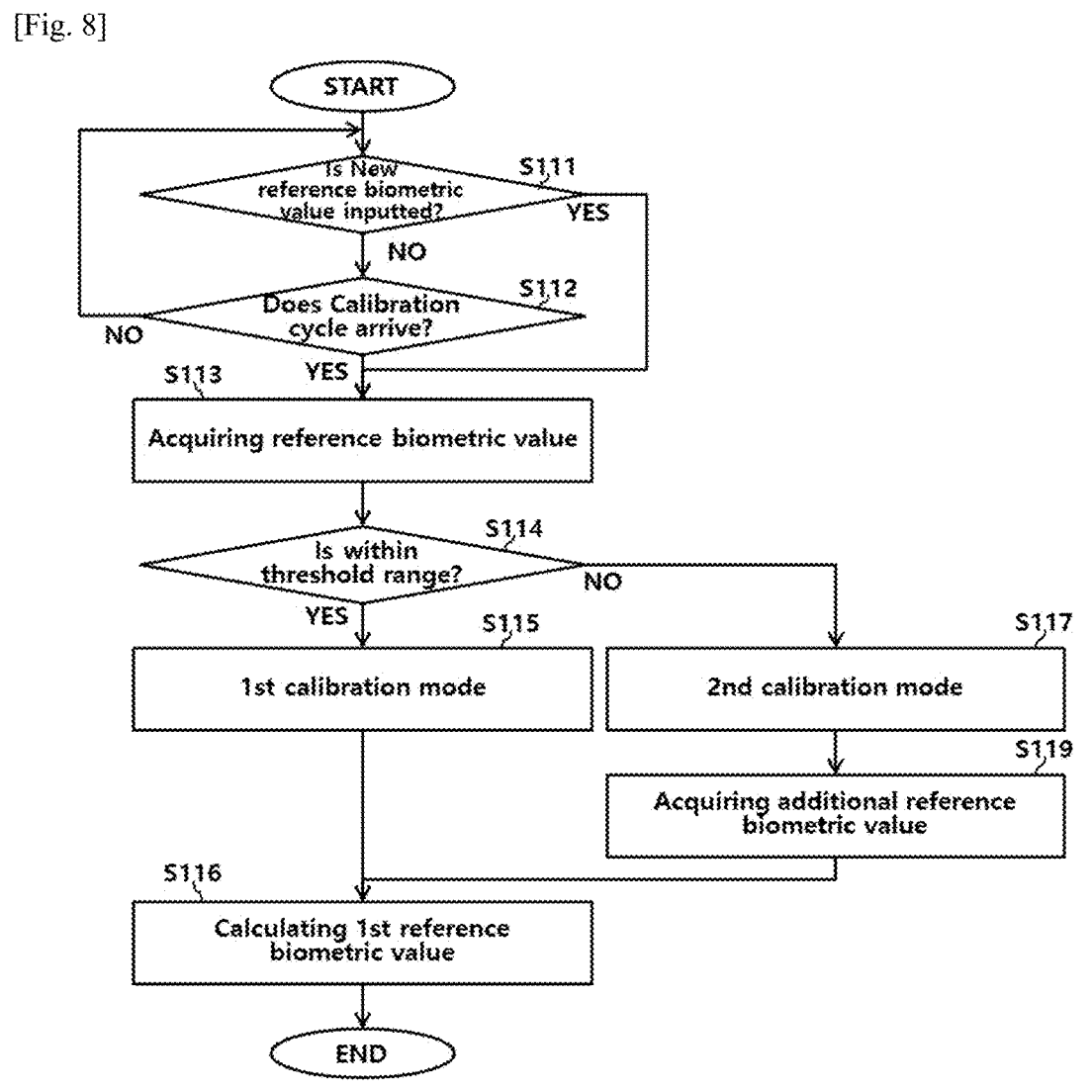

FIG. 8 is a flowchart for explaining a method for obtaining a first reference biometric value according to an embodiment of the present disclosure.

Describing in more detail with reference to FIG. 8, whether a new reference biometric value has been input by a user's request is determined (S111). Normally, the new reference biometric value is inputted every calibration period, but the new reference biometric value for calculating a calibration sensitivity may be inputted at the user's request even before the calibration period arrives.

If a new reference biometric value is not inputted by the user's request, whether the set calibration period has arrived is determined (S112). If the set calibration period arrives, a message for requesting a new reference biometric value at the first time point when the calibration period arrives is outputted to the user to obtain a reference biometric value measured by a biometric information meter at the first time point (S113).

A difference value is calculated by calculating difference between a measured biometric value calculated from biometric information measured at the first time point by the sensor transmitter using the calibration sensitivity used up to the first time point and the reference biometric value at the first time point, and whether the calculated difference value is within a threshold range is determined (S114).

If the difference value is within the threshold range, the first mode is chosen (S115), and the reference biometric value obtained at the first time point is calculated as the first reference biometric value (S116).

However, when the difference value is out of the threshold range, the second mode is chosen (S117), and at least one additional reference biometric value is acquired through the biometric information meter after the first time point (S119). When the second mode is used or chosen, an average value of the reference biometric value at the first time point and the additional reference biometric value is calculated as the first reference biometric value (S116).

FIG. 9 is a diagram for explaining a time point when a calibration sensitivity is generated, and as shown in FIG. 9(a), a first sensitivity is calculated from a first reference biometric value for each set calibration period ($T_P$) and a new calibration sensitivity is generated from the first sensitivity and at least one piece of past sensitivity information.

In addition to the set calibration cycle, a calibration sensitivity can be generated before the calibration cycle set by the user's request arrives, and as illustrated in FIG. 9(b), a first reference biometric value is obtained by the user's request at time t2' before the set calibration period arrives, a first sensitivity is calculated from the first reference biometric value, and a new calibration sensitivity is generated from the first sensitivity and at least one piece of past sensitivity information. The time point at which the new calibration sensitivity is generated is initialized to the set calibration cycle, and then, a new calibration sensitivity is generated at the set calibration cycle.

FIG. 10 illustrates an example of a user interface screen displayed on a user terminal to select a calibration mode according to another embodiment of the present disclosure.

As shown in FIG. 10(a), an input window for inputting a reference biometric value measured by the biometric information meter at the first time point of the calibration cycle is activated.

As shown in FIG. 10(b), when the difference between the reference biometric value input into the input window and the measured biometric value is out of a first threshold range, a separate input window for inputting a plurality of reference biometric values measured at different times after the first time point is activated. According to the field to which the present disclosure is applied, one or more separate input windows may be activated. When a plurality of reference biometric values measured at different times are inputted, a first reference biometric value is obtained using the plurality of reference biometric values.

Meanwhile, the exemplary embodiments of the present disclosure described above can be implemented through programs executable at computers, and can be operated in a general-purpose digital computer executing the programs using computer readable medium.

The above-referenced computer readable medium comprises storage medium such as magnetic storage media (e.g., ROM, floppy disks, hard disks, etc.), optical recording media (e.g., CD-ROMs, DVDs, etc.), and carrier waves (e.g., transmission through the Internet).

Although the present disclosure is described with reference to embodiments shown in the drawings in order to explain certain principles of the present disclosure by way of example, a person having ordinary skill in the art which the present disclosure relates could make various modifications and equivalent other embodiments. Accordingly, the protection scope of the present disclosure shall be defined by the claims attached hereto and all of their equivalents.

What is claimed is:

1. A method for calculating a calibration sensitivity of a sensor for insertion into a body, the method comprising:
   acquiring a first reference biometric value indicating a biometric state of a user at a first time point, and calculating a first sensitivity from a ratio of biometric information measuring the biometric state of the user using the sensor for insertion into the body at the first time point and the first reference biometric value;
   retrieving past sensitivity information which has been prestored and used before the first time point;
   calculating the calibration sensitivity for calibrating the biometric information measured through the sensor for insertion into the body after the first time point from the first sensitivity and the past sensitivity information; and
   continuously calibrating the biometric information measured through the sensor while the senser is being inserted into the body,
   wherein the past sensitivity information is at least one calibration sensitivity randomly selected from calibration sensitivities which had been used for a past set time period based on the first time point or at least one sensitivity randomly selected from sensitivities which had been calculated for the past set time period based on the first time point.

2. The method for calculating the calibration sensitivity of the sensor for insertion into the body according to claim 1, wherein the past sensitivity information is at least one calibration sensitivity which was used before the first time point or at least one sensitivity which was calculated before the first time point.

3. The method for calculating the calibration sensitivity of the sensor for insertion into the body according to claim 2, wherein the past sensitivity information is at least one calibration sensitivity which was used continuously just before the first time point or at least one sensitivity which was calculated just before the first time point.

4. The method for calculating the calibration sensitivity of the sensor for insertion into the body according to claim 2, wherein the calculating of the first sensitivity comprises:
   acquiring the first reference biometric value of the user indicating the biometric state of the user through a test strip at the first time point;

determining the biometric information measured through the sensor for insertion into the body at the first time point; and
   calculating the first sensitivity based on a ratio of the biometric information and the first reference biometric value.

5. The method for calculating the calibration sensitivity of the sensor for insertion into the body according to claim 4, wherein a difference between a biometric value of the user, calculated from the biometric information using the past calibration sensitivity, and the first reference biometric value is calculated, and if the difference is out of a threshold range, the acquired first reference biometric value is removed.

6. The method for calculating the calibration sensitivity of the sensor for insertion into the body according to claim 4, wherein, in the acquiring of the first reference biometric value, one calibration mode among a first calibration mode and a second calibration mode is selected based on whether the difference between the biometric value of the user, calculated from the biometric information using the past calibration sensitivity, and the first reference biometric value is out of the threshold range.

7. The method for calculating the calibration sensitivity of the sensor for insertion into the body according to claim 6, wherein:
   when the difference is within the threshold range, the first calibration mode is selected, and
   in the first calibration mode, one reference biometric value measured through the test strip at the first time point is acquired as the first reference biometric value.

8. The method for calculating the calibration sensitivity of the sensor for insertion into the body according to claim 6, wherein:
   when the difference is out of the threshold range, the second calibration mode is selected, and
   in the second calibration mode, one or more additional reference biometric values are additionally acquired through the test strip continuously after the first time point, and the first reference biometric value is acquired from the reference biometric value acquired at the first time point and an average value of the one or more additional reference biometric values.

9. The method for calculating the calibration sensitivity of the sensor for insertion into the body according to claim 2, wherein the calibration sensitivity is calculated as an average value of the first sensitivity and the past sensitivity information.

10. The method for calculating the calibration sensitivity of the sensor for insertion into the body according to claim 2, wherein, when a new reference biometric value is acquired after the first time point, the first sensitivity is stored and a calibration sensitivity is newly calculated using the stored first sensitivity as a past sensitivity.

11. The method for calculating the calibration sensitivity of the sensor for insertion into the body according to claim 10, further comprising:
   determining whether a calibration cycle set after the first time point arrives, and
   when the set calibration cycle arrives, outputting a request message for requesting to input the new reference biometric value,
   wherein, when the new reference biometric value is acquired in response to the request message, the first sensitivity is stored and the calibration sensitivity is newly calculated using the stored first sensitivity as the past sensitivity.

* * * * *